United States Patent
Himeda et al.

(10) Patent No.: US 9,315,381 B2
(45) Date of Patent: *Apr. 19, 2016

(54) DEHYDROGENATION CATALYST FOR FORMIC ACID, METHOD FOR PRODUCING HYDROGEN, AND METHOD FOR PRODUCING HEAVY-HYDROGEN GAS OR HEAVY-HYDROGENATED HYDROGEN

(71) Applicant: National Institute of Advanced Industrial Science and Technology, Tokyo (JP)

(72) Inventors: Yuichiro Himeda, Ibaraki (JP); Wan-Hui Wang, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/374,012

(22) PCT Filed: Jan. 25, 2013

(86) PCT No.: PCT/JP2013/051606
§ 371 (c)(1),
(2) Date: Jul. 23, 2014

(87) PCT Pub. No.: WO2013/111860
PCT Pub. Date: Aug. 1, 2013

(65) Prior Publication Data
US 2015/0166337 A1 Jun. 18, 2015

(30) Foreign Application Priority Data
Jan. 27, 2012 (JP) ................. 2012-015087

(51) Int. Cl.
| | |
|---|---|
| *H01M 8/06* | (2006.01) |
| *C01B 3/22* | (2006.01) |
| *B01J 31/22* | (2006.01) |
| *C01B 3/32* | (2006.01) |
| *B01J 31/18* | (2006.01) |
| *C01B 4/00* | (2006.01) |
| *C07F 15/00* | (2006.01) |

(52) U.S. Cl.
CPC ............. *C01B 3/326* (2013.01); *B01J 31/1815* (2013.01); *B01J 31/2295* (2013.01); *C01B 3/22* (2013.01); *C01B 4/00* (2013.01); *C07F 15/0033* (2013.01); *B01J 2231/763* (2013.01); *B01J 2531/005* (2013.01); *B01J 2531/0205* (2013.01); *B01J 2531/0216* (2013.01); *B01J 2531/821* (2013.01); *B01J 2531/822* (2013.01); *B01J 2531/827* (2013.01); *C01B 2203/02* (2013.01); *C01B 2203/0277* (2013.01); *C01B 2203/1041* (2013.01); *C01B 2203/1211* (2013.01); *H01M 8/065* (2013.01)

(58) Field of Classification Search
CPC ............ B01J 10/00; B01J 23/78; B01J 23/84; B01J 2531/0216; B01J 31/2295; B01J 2231/763; B01J 2531/27; B01J 2531/0205; B01J 2531/005; B01J 2531/822; B01D 53/62; C07D 403/04; C01B 2203/1211; C01B 2203/1041; C01B 2203/02; C01B 3/326; C01B 4/00; C01B 3/22; C07F 15/0033; H01M 8/065
USPC ....................................... 514/252.02; 544/238
See application file for complete search history.

(56) References Cited

U.S. PATENT DOCUMENTS

| | | |
|---|---|---|
| 2010/0034733 A1 | 2/2010 | Fukuzumi et al. |
| 2010/0068131 A1 | 3/2010 | Laurenczy et al. |
| 2010/0168120 A1* | 7/2010 | Watterson et al. ....... 514/252.02 |
| 2012/0321550 A1 | 12/2012 | Fukuzumi et al. |
| 2013/0338159 A1* | 12/2013 | Cornella Taracido et al. .................. 514/235.8 |
| 2014/0299817 A1 | 10/2014 | Hull et al. |

Catalyst (4) : 0.5 μmol, Reaction temperature 60°C
1 M HCOOH/HCOONa (1:1) 10 mL

FOREIGN PATENT DOCUMENTS

| | | |
|---|---|---|
| JP | 3968431 | 6/2007 |
| JP | 4009728 | 9/2007 |
| JP | 2010-064011 | 3/2010 |
| JP | 2010-506818 | 3/2010 |
| JP | 2010-083730 | 4/2010 |
| JP | 2010-208927 | 9/2010 |
| JP | 2010208927 A * | 9/2010 |
| JP | 4572393 | 11/2010 |
| JP | 4822253 | 9/2011 |
| JP | 2015-502914 | 1/2015 |
| WO | 2008/059630 | 5/2008 |
| WO | 2011/108730 | 9/2011 |
| WO | 2013040013 | 3/2013 |

OTHER PUBLICATIONS

Himeda "Highly efficient hydrogen evolution by decomposition of formic acid using an iridium catalyst with 4, 4'-dihydroxy-2,2'-bipyridine" 2009, Green Chemistry, 11, 2018-2022.*
U.S. Appl. No. 61/533,950, filed Sep. 13, 2011.
Boddien, A. et al., "Efficient Dehydrogenation of Formic Acid Using an Iron Catalyst," Science, vol. 333, Sep. 23, 2011, pp. 1733-1736.
Papp, G. et al., "A Charge/Discharge Device for Chemical Hydrogen Storage and Generation," Angew. Chem. Int. Ed., vol. 50, 2011, pp. 10433-10435.
Tanaka, R. et al., "Mechanistic Studies on the Reversible Hydrogenation of Carbon Dioxide Catalyzed by an Ir-PNP Complex," Organometallics 2011, vol. 30, pp. 6742-6750.
Himeda, Y., "Highly Efficient Hydrogen Evolution by Decomposition of Formic Acid Using an Iridium Catalyst with 4,4'-dihydroxy-2,2'-bipyridine," Green Chem., vol. 11, 2009, pp. 2018-2022.
Himeda, Y. et al., "Interconversion between Formic Acid and $H_2/Co_2$ using Rhodium and Ruthenium Catalysts for $CO_2$ Fixation and $H_2$ Storage," ChemSusChem, 2011, vol. 4, pp. 487-493.
Himeda, Y. et al., "Transfer Hydrogenation of a Variety of Ketones Catalyzed by Rhodium Complexes in Aqueous Solution and their Application to Asymmetric Reduction Using Chiral Schiff Base Ligands," Journal of Molecular Catalysis A: Chemical, 2003, vol. 195, pp. 95-100.
Himeda, Y. et al., "Half-Sandwich Complexes with 4,7-Dihydroxy-1,10-phenanthroline: Water-Soluble, Highly Efficient Catalysts for Hydrogenation of Bicarbonate Attributable to the Generation of an Oxyanion on the Catalyst Ligand," Organometallics 2004, vol. 23, pp. 1480-1483.
Sajiki, H. et al., "Complete Replacement of $H_2$ by $D_2$ via Pd/C-Catalyzed H/D Exchange Reaction," Organic Letters 2004, vol. 6, No. 20, pp. 3521-3523.
Fukuzumi, S. et al., "Efficient Catalytic Decomposition of Formic Acid for the Selective Generation of $H_2$ and H/D Exchange with a Water-Soluble Rhodium Complex in Aqueous Solution," ChemSusChem 2008, vol. 1, pp. 827-834.
Fukuzumi, S. et al., "Unusually Large Tunneling Effect on Highly Efficient Generation of Hydrogen and Hydrogen Isotopes in pH-Selective Decomposition of Formic Acid Catalyzed by a Heterodinuclear Iridium—Ruthenium Complex in Water," J. Am. Chem. Soc. 2010, vol. 132, pp. 1496-1497.
Himeda, Y. et al., "Catalytic (transfer) Deuterogenation in $D_2O$ as deuterium source with $H_2$ and $HCO_2H$ as Electron Sources," Dalton Transactions, 2009, pp. 6286-6288.
Govindaswamy, P. et al., "Mono and Dinuclear Rhodium, Iridium and Ruthenium Complexes Containing Chelating 2,2'-bipyrimidine Ligands: Synthesis, Molecular Structure, Electrochemistry and Catalytic Properties," Journal of Organometallic Chemistry, vol. 692, 2007, pp. 3664-3675.
Kaim, W. et al., "Coupling of Electron Transfer and Bond Dissociation Processes in Dinuclear Complexes with Rhodium and Iridium Reaction Centres Bridged by 2,2'-bipyrimidine", Collection of Czechoslovak Chemical Communications, 66(2) (2001).

* cited by examiner

*Primary Examiner* — Stanley Silverman
*Assistant Examiner* — Syed Iqbal
(74) *Attorney, Agent, or Firm* — Carmody Torrance Sandak & Hennessey LLP

(57) ABSTRACT

To provide a catalyst for dehydrogenation of formic acid which allows hydrogen, heavy hydrogen gas or heavy-hydrogenated hydrogen containing no carbon monoxide to be produced through dehydrogenation of formic acid in a highly efficient manner.
A catalyst for dehydrogenation of formic acid, including:
a multinuclear metal complex represented by the following Formula (1), a tautomer or stereoisomer thereof, or a salt thereof,

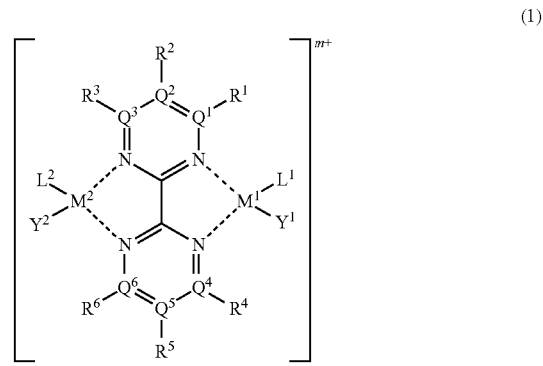

(1)

where
$M^1$ and $M^2$ denote transition metals and may be the same as or different from each other;
$Q^1$ to $Q^6$ each independently denote carbon or nitrogen;
$R^1$ to $R^6$ each independently denote, for example, a hydrogen atom, an alkyl group, a phenyl group, a nitro group, a halogen group, a sulfonate group (sulfo group);
$L^1$ and $L^2$ each independently denote an aromatic anionic ligand or an aromatic ligand, and may be substituted by one or more substituents;
$Y^1$ and $Y^2$ each independently denote any ligand or are absent; and
m denotes a positive integer, 0, or a negative integer.

17 Claims, 2 Drawing Sheets

Catalyst (4) : 0.5 μmol, Reaction temperature 60°C
1 M HCOOH/HCOONa (1:1) 10 mL

Catalyst (4): 0.5 umol, Reaction temperature 60°C

An aqueous solution (10 mL) of which pH has been adjusted with 1M HCOOH/HCOONa

Catalyst (4): 1 mmol, Reaction temperature 60°C
Pressure inside a sealed glass autoclave containing an aqueous solution of 1M HCOOH (10 mL)

DEHYDROGENATION CATALYST FOR FORMIC ACID, METHOD FOR PRODUCING HYDROGEN, AND METHOD FOR PRODUCING HEAVY-HYDROGEN GAS OR HEAVY-HYDROGENATED HYDROGEN

TECHNICAL FIELD

The present invention relates to a method for producing hydrogen using a catalyst for dehydrogenation of formic acid, and a method for producing heavy hydrogen gas or heavy-hydrogenated hydrogen using heavy water and heavy formic acid.

BACKGROUND ART

Hydrogen ($H_2$) has been produced in an amount of about five hundred billion $Nm^3$ all over the world. The hydrogen has attracted much attention as future clean energy as well as has been applied for a variety of uses such as refinement of oil or production of ammonia. For example, a fuel cell is capable of efficiently supplying electricity when the hydrogen is supplied externally thereto.

However, the hydrogen is highly reactive gas, so that it is difficult to be transported and stored. Therefore, there has been a need for a safe and inexpensive transportation and storage technology in order to stably supply the hydrogen. In the field of the fuel cell, there has been a problem that a poisoning substance is by-produced on a surface of an electrode catalyst by the action of carbon monoxide. Thus, there has been a need to supply high purity hydrogen generally containing 10 ppm or less of carbon monoxide.

As a hydrogen storage method, at present, a method for storing hydrogen as high pressure gas in a gas cylinder is commonly used. However, in this method, there are problems of safety upon transportation of the high pressure gas, and hydrogen brittleness of container materials. A method for storing hydrogen gas in the form of liquid hydrogen under extremely low temperature is also used. However, there have been problems that much energy is consumed in a liquefaction process and that the liquid hydrogen is lost in a percentage of 3% per day to 6% per day due to vaporization.

In order to solve the above described problems with regard to hydrogen transportation and storage technologies, there has been considered a method for storing hydrogen as liquid fuel (e.g., methanol and formic acid) which is obtained by hydrogenating carbon dioxide. For example, formic acid (HCOOH) has recently been attracted the attention as a hydrogen storage material since the formic acid, which is in the liquid form at normal temperature and has a relatively low toxicity, can be decomposed into hydrogen ($H_2$) and carbon dioxide ($CO_2$). However, there has been a problem that thermal decomposition of the formic acid using a conventionally known catalyst requires high temperature of 200° C. or higher, and generates carbon monoxide as a by-product. Therefore, there has been a need to develop a catalyst which allows hydrogen to be selectively and efficiently produced from formic acid under a mild condition, and, if necessary, allows high pressure hydrogen to be supplied.

Recently, many catalysts for dehydrogenation of formic acid containing metal complexes have been reported with regard to a hydrogen production technology almost without by-producing carbon monoxide (PTLs 1 to 3 and NPLs 1 and 2). The catalysts can act under a relatively mild reaction condition, but they have an only low activity, which is problematic. Very recently, one of the catalysts left a record of 120,000 in the turnover frequency per hour at 80° C. However, the catalyst was reacted for only 1 min, and required an amine additive in alcohol, so that it is a long way from practical use (NPL 3). Apart from the above reports, the present inventors have found a catalyst for dehydrogenation of formic acid to be used in water. However, there have remained problems with regard to catalyst activity and catalyst durability which are unsatisfactory for practical use, and the use of an expensive catalyst ligand (PTLs 4 to 6 and NPLs 4 to 7).

Recently, the present inventors has been found an epoch-making catalyst which allows hydrogen to be highly efficiently and highly selectively produced through dehydrogenation of formic acid in water (turnover frequency per hour: 230,000; reaction temperature: 90° C.) under a mild reaction condition without using an organic additive in a cooperative research with Brookhaven National Laboratory in USA (PTL 7). However, there has remained an economic problem since this catalyst contains a catalyst ligand which is synthesized in a complicated manner.

On the other hand, there has been considered that a catalyst for dehydrogenation of formic acid is applied to a technology for producing heavy hydrogen gas which is used for producing an expensive heavy-hydrogenated compound. The heavy-hydrogenated compound has been widely utilized as, for example, a label compound in investigation of a mechanism of a reaction through tracing the reaction or in structural analysis of a biological substance. Recently, it has also attracted the interest as pharmaceuticals, agricultural chemicals, organic EL materials, or optical fibers. However, production of the heavy-hydrogenated compound has conventionally needed to include a number of steps, so that the resultant heavy-hydrogenated compound was very expensive, and only limited types of heavy-hydrogenated compounds were obtained. Extremely expensive deuterium gas ($D_2$) is generally used for synthesizing the heavy-hydrogenated compound. Currently, the heavy-hydrogenated gas is produced by electrolysis of heavy water, but application thereof at a laboratory scale is restricted by its extremely high cost.

On the contrary, it has been known that the heavy hydrogen gas ($D_2$, $T_2$) can be produced from hydrogen gas ($H_2$) and heavy water ($D_2O$, $T_2O$), which are both easily available, through an H/D exchange reaction. However, there has been a problem that a time-consuming pretreatment is needed (NPL 8). There has been considered, as a one of technologies for producing the heavy hydrogen gas, a method for producing heavy hydrogen by utilizing a catalyst for dehydrogenation of heavy formic acid in heavy water. However, this technology has a problem that the reaction rate is extremely slow, so that it has remained mere a theoretical examination.

There has been attempted a method for producing hydrogen isotope gas through dehydrogenation of formic acid from an aqueous solution of formic acid in which any one of water and formic acid (formic acid salt) has been heavy-hydrogenated. However, there has not been reported that satisfactory catalyst performance is achieved (PTLs 8 and 9 and NPLs 9 to 11).

Under the above described circumstances, there has been a need for a method for producing high purity heavy hydrogen gas in an inexpensive and easier manner.

NPL 12 describes a multinuclear catalyst for production of alcohols through reduction of ketones using formic acid. However, the turnover frequency per hour of the catalyst was very low, i.e., up to 20, so that the catalyst is never expected to be used as a catalyst for dehydrogenation of formic acid.

CITATION LIST

Patent Literature

PTL 1: Japanese Patent (JP-B) No. 4572393
PTL 2: International Publication No. WO2011/108730A1
PTL 3: Japanese Patent Application Laid-Open (JP-A) No. 2010-506818
PTL 4: JP-B No. 3968431
PTL 5: JP-B No. 4009728
PTL 6: JP-B No. 4822253
PTL 7: U.S. provisional patent application No. 61-533950
PTL 8: JP-A No. 2010-83730
PTL 9: JP-A No. 2010-64011

Non-Patent Literature

NPL 1: Boddien, A.; Mellmann, D.; Gaertner, F.; Jackstell, R.; Junge, H.; Dyson, P. J.; Laurenczy, G.; Ludwig, R.; Beller, M. Science 2011, 333, 1733.
NPL 2: Papp, G.; Csorba, J.; Laurenczy, G.; Joo, F. Angew. Chem.-Int. Edit. 2011, 50, 10433.
NPL 3: Tanaka, R.; Yamashita, M.; Chung, L. W.; Morokuma, K.; Nozaki, K. Organometallics 2011, 30, 6742.
NPL 4: Himeda, Y. Green Chem. 2009, 11, 2018.
NPL 5: Himeda, Y. Miyazawa, S.; Hirose, T. Chem Sus Chem 2011, 4, 487.
NPL 6: Himeda, Y.; Onozawa-Komatsuzaki, N.; Sugihara, H.; Arakawa, H.; Kasuga, K. J. Mol. Catal. A-Chem. 2003, 195, 95.
NPL 7: Himeda, Y.; Onozawa-Komatsuzaki, N.; Sugihara, H.; Arakawa, H.; Kasuga, K. Organometallics 2004, 23, 1480.
NPL 8: Sajiki, H.; Kurita, T.; Esaki, H.; Aoki, F.; Maegawa, T.; Hirota, K. Org. Lett. 2004, 6, 3521.
NPL 9: Fukuzumi, S.; Kobayashi, T.; Suenobu, T. Chem Sus Chem 2008, 1, 827.
NPL 10: Fukuzumi, S.; Kobayashi, T.; Suenobu, T. J. Am. Chem. Soc. 2010, 132, 1496.
NPL 11: Himeda, Y.; Miyazawa, S.; Onozawa-Komatsuzaki, N.; Hirose, T.; Kasuga, K. Dalton Trans. 2009, 6286.
NPL 12: Govindaswamy, P.; Canivet, J.; Therrien, B.; Suss-Fink, G.; Stepnicka, P.; Ludvik, J. J. Organomet. Chem. 2007, 692, 3664.

SUMMARY OF INVENTION

Technical Problem

An object of the present invention is to provide a catalyst for dehydrogenation of formic acid which allows hydrogen ($H_2$), heavy hydrogen gas ($D_2$, $T_2$), or heavy-hydrogenated hydrogen (HD, HT) containing no carbon monoxide to be highly efficiently produced through dehydrogenation of formic acid.

Another object of the present invention is to provide a method for producing heavy hydrogen gas ($D_2$, $T_2$) or heavy-hydrogenated hydrogen (HD, HT) using heavy water and/or heavy formic acid in a highly efficient, simple, and inexpensive manner.

A still another object of the present invention is to provide a method for producing pressurized hydrogen such as high pressure hydrogen so as to stably and continuously supply hydrogen in a required amount to a hydrogen consuming device such as a fuel cell.

Solution to Problem

The present inventors conducted extensive studies to solve the above-described problems and consequently have found that a multinuclear metal complex represented by the following Formula (1) is useful as a catalyst for dehydrogenation of formic acid, to thereby complete the present invention. The present invention is composed of the following technical means:

[1] A catalyst for dehydrogenation of formic acid, including:
a multinuclear metal complex represented by the following Formula (1), a tautomer or stereoisomer thereof, or a salt thereof,

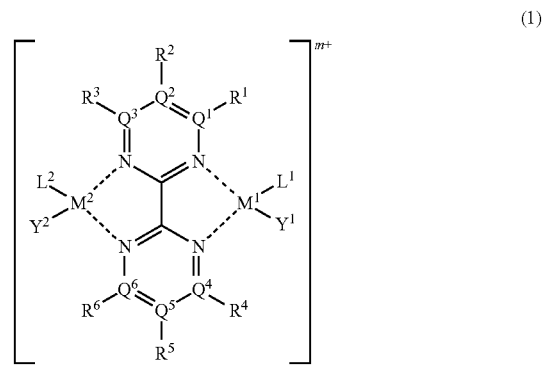

(1)

where
$M^1$ and $M^2$ denote transition metals and may be the same as or different from each other;
$Q^1$ to $Q^6$ each independently denote carbon or nitrogen;
$R^1$ to $R^6$ each independently denote a hydrogen atom, an alkyl group, a phenyl group, a nitro group, a halogen group, a sulfonate group (sulfo group), a carboxylate group (carboxy group), an alkoxy group, an alkyl amino group, provided that when $Q^i$ is nitrogen, $R^i$ is absent at a position corresponding to the nitrogen;
$L^1$ and $L^2$ each independently denote an aromatic anionic ligand or an aromatic ligand, and may be unsubstituted or substituted by one or more substituents;
$Y^1$ and $Y^2$ each independently denote any ligand or are absent; and
m denotes a positive integer, 0, or a negative integer.

[2] The catalyst for dehydrogenation of formic acid according to [1], wherein $M^1$ and $M^2$ each independently denote iridium, rhodium, ruthenium, cobalt, osmium, nickel, iron, palladium or platinum.

[3] The catalyst for dehydrogenation of formic acid according to [1], wherein $M^1$ and $M^2$ denote iridium.

[4] The catalyst for dehydrogenation of formic acid according to any one of [1] to [3], wherein $L^1$ and $L^2$ each independently denote pentamethylcyclopentadienyl or hexamethylbenzene.

[5] The catalyst for dehydrogenation of formic acid according to any one of [1] to [4], wherein $Y^1$ and $Y^2$ each independently denote a water molecule, a hydrogen atom, a heavy hydrogen atom, an alkoxide ion, a hydroxide ion, a halide ion, a carbonate ion, a trifluoromethanesulfonate ion, a sulfate ion, a nitrate ion, a formate ion, or an acetate ion, or are absent.

[6] The catalyst for dehydrogenation of formic acid according to any one of [1] to [5], wherein the multinuclear metal complex represented by the Formula (1) is a multinuclear metal complex having a structure represented by the following Formula (2), (2)

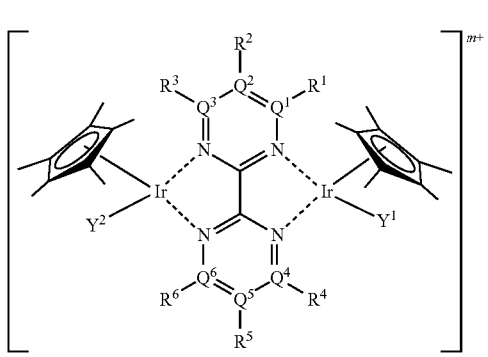

where
Q¹ to Q⁶, R¹ to R⁶, Y¹, Y² and m are the same as in the Formula (1).

[7] The catalyst for dehydrogenation of formic acid according to [6], wherein all of Q¹ to Q⁶ denote carbon atoms.

[8] The catalyst for dehydrogenation of formic acid according to [6], wherein all of R¹ to R⁶ denote hydrogen atoms.

[9] The catalyst for dehydrogenation of formic acid according to [6], wherein the multinuclear metal complex represented by the Formula (2) is a multinuclear metal complex represented by the following Formula (3), (3)

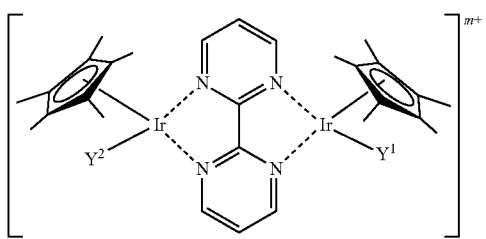

where
Y¹, Y² and m are the same as in the Formula (2).

[10] The catalyst for dehydrogenation of formic acid according to [9], wherein the multinuclear metal complex represented by the Formula (3) is one or more of multinuclear metal complexes represented by the following Formulae (4) to (10), (4)

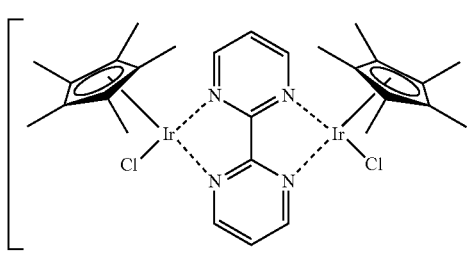

(5)

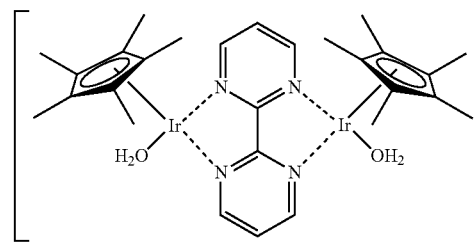

(6)

(7)

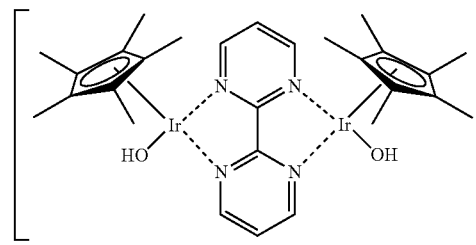

(8)

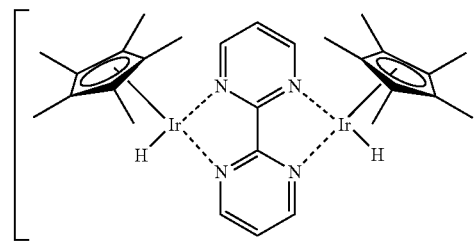

(9)

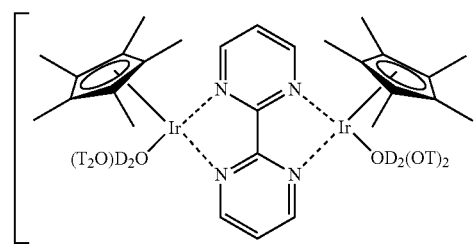

(10)

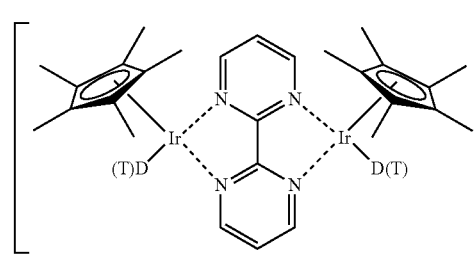

[11] A method for dehydrogenating formic acid, including:
allowing a solution containing formic acid and/or a formic acid salt to react in the presence of the catalyst for dehydrogenation of formic acid according to any one of [1] to [10], to thereby dehydrogenate formic acid.

[12] A method for producing hydrogen gas ($H_2$) through dehydrogenation xof formic acid, including:
allowing a solution containing formic acid and/or a formic acid salt to react in the presence of the catalyst for dehydrogenation of formic acid according to any one of [1] to [10], to thereby produce hydrogen gas ($H_2$).

[13] The method for dehydrogenating formic acid according to [11], wherein heavy hydrogen gas ($D_2$, $T_2$), heavy-hydrogenated hydrogen gas (HD, HT), or both thereof is produced using deuterium water ($D_2O$) and/or tritium water ($T_2O$) as a solvent of the solution.

[14] The method for dehydrogenating formic acid according to [11], wherein heavy hydrogen gas ($D_2$, $T_2$), heavy-hydrogenated hydrogen gas (HD, HT), or both thereof is produced using deuterated formic acid (DCOOD) as the formic acid and/or deuterated formic acid salt (DC001 as the formic acid salt.

[15] The method for dehydrogenating formic acid according to [11], wherein heavy hydrogen gas ($D_2$, $T_2$) is produced using deuterated formic acid (DCOOD) as the formic acid and/or deuterated formic acid salt ($DCOO^-$) as the formic acid salt, and deuterium water ($D_2O$) and/or tritium water ($T_2O$) as the solvent.

[16] The method for producing hydrogen gas ($H_2$), heavy hydrogen gas ($D_2$, $T_2$), or heavy-hydrogenated hydrogen gas (HD, HT) according to any one of [12] to [15], wherein a pH of a reaction solution is varied.

[17] The method for producing hydrogen gas ($H_2$), heavy hydrogen gas ($D_2$, $T_2$), or heavy-hydrogenated hydrogen gas (HD, HT) according to any one of [12] to [15], wherein the hydrogen gas ($H_2$), the heavy hydrogen gas ($D_2$, $T_2$), or the heavy-hydrogenated hydrogen gas (HD, HT) pressurized in a reaction container of which internal pressure is 0.1 MPa or more is produced.

Advantageous Effects of Invention

A catalyst for dehydrogenation of formic acid of the present invention allows hydrogen ($H_2$) to be produced from a hydrogen storage material, formic acid, and allows heavy hydrogen gas ($D_2$, $T_2$) and/or heavy-hydrogenated hydrogen (HD, HT) to be produced from heavy formic acid and/or heavy water in a highly efficiently manner without by-producing carbon monoxide which poisons a catalyst for, for example, a fuel cell.

The present invention also allow hydrogen isotope gas, which has been conventionally stored in, for example, a gas cylinder, to be stored in formic acid in the liquid form, which results in an extremely easy transportation and storage of the hydrogen isotope gas.

Additionally, a catalyst for dehydrogenation of formic acid of the present invention can be very inexpensively produced since it can be prepared with a catalyst ligand which is more inexpensively available than the catalyst described in PTL 7 while it has epoch-makingly excellent catalyst performance which is equivalent to that of the catalyst described in PTL 7.

DESCRIPTION OF EMBODIMENTS

Figure 1:
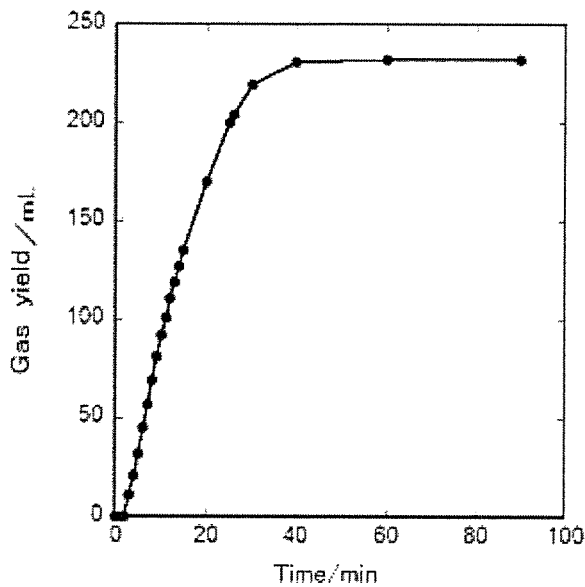
FIG. 1 is a graph representing a change in a gas yield over time in an aqueous solution of 1 M formic acid/sodium formate (1:1) containing a catalyst for dehydrogenation of formic acid of Example.

As used herein, heavy hydrogen means deuterium (D) or tritium (T); heavy-hydrogenation means deuteration and tritiation; and hydrogen isotope gas means heavy hydrogen gas ($D_2$, $T_2$) and heavy-hydrogenated hydrogen (HD, HT). Formic acid and/or a formic acid salt refers to the formic acid alone, the formic acid salt alone, a mixture of the formic acid with the formic acid salt, or a mixture of the formic acid or the formic acid salt with an acid or a base. Heavy formic acid and/or heavy formic acid salt has the same meaning as in the above sentence.

In the present invention, a dehydrogenation reaction of formic acid represented by the following scheme highly efficiently generates hydrogen and carbon dioxide. During the reaction, there is a possibility that carbon monoxide and water are by-produced due to a decarbonylation reaction. However, a catalyst for dehydrogenation of formic acid of the present invention allows hydrogen gas containing no carbon monoxide to be produced under a mild condition in a highly selective and highly efficient manner.

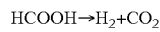

$HCOOH \rightarrow H_2 + CO_2$

In the present invention, heavy hydrogen gas ($D_2$, $T_2$), heavy-hydrogenated hydrogen (HD, HT), or both thereof can be produced in a highly efficient manner through a dehydrogenation reaction of formic acid represented by the following scheme in the case where heavy water and/or heavy formic acid and/or heavy formic acid salt are used.

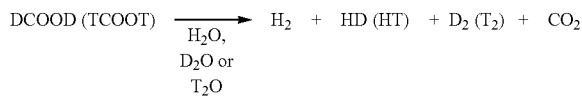

In the present invention, the heavy hydrogen gas ($D_2$, $T_2$), the heavy-hydrogenated hydrogen (HD, HT), or both thereof can be produced in a highly efficient manner through a dehydrogenation reaction of formic acid represented by the following scheme in the case where formic acid and/or formic acid salt in the heavy water are used.

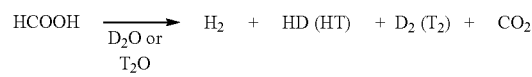

In the complex represented by the General Formula (1), examples of the transition metal M include iridium, rhodium, ruthenium, cobalt, osmium, nickel, iron, palladium or platinum. Particularly preferred is iridium.

In the complex represented by the General Formula (1), the substituents $R^1$ to $R^6$ are each independently a hydrogen atom, an alkyl group, a phenyl group, a nitro group, a halogen group, a sulfonate group (sulfo group), a carboxylate group (carboxy group), an alkoxy group, or an alkyl amino group, provided that when $Q^i$ is nitrogen, $R^i$ is absent at a position corresponding to the nitrogen.

In the complex represented by the General Formula (1), examples of the elements $Q^1$ to $Q^6$ include carbon or nitrogen. Particularly preferably, all of the elements are carbon.

In the complex represented by the General Formula (1), $L^1$ and $L^2$ are an aromatic anionic ligand or an aromatic ligand, and may be substituted or unsubstituted. Preferably, they are a cyclopentadienyl ligand or a benzene ligand, and may be substituted or unsubstituted. They may be substituted with an alkyl group, an aromatic group, a hydroxyl group (—OH), an ester group (—COOR), an amide group (—CONRR'), a halogen atom (—X), an alkoxy group (—OR), an alkylthio group (—SR), an amino group (—NRR'), a carboxylate group (—COOH), a nitro group, or a sulfonate group (—SO$_3$H), which may be same as or different from each other. Particularly preferred is a pentamethylcyclopentadienyl ligand or a hexamethylbenzene ligand in which all of substituents are methyl groups.

In the complex represented by the General Formula (1) or (2), the ligands $Y^1$ and $Y^2$ may be a ligand of a hydrogen atom (—H), a heavy hydrogen atom (-D, -T), a water molecule (—OH$_2$), a heavy water molecule (—OD$_2$, —OT$_2$), a hydroxide ion (—OH), a heavy-hydrogenated hydroxide ion (—OD, —OT), an alkoxide ion, a halide ion, a carbonate ion, a sulfate ion, a nitrate ion, an acetate ion, or a formate ion, or may be absent. The alkoxide ion is not particularly limited. Examples thereof include an alkoxide ion derived from, for example, methanol, ethanol, n-propyl alcohol, isopropyl alcohol, n-butyl alcohol, sec-butyl alcohol, isobutyl alcohol, or tert-butyl alcohol.

In the complex represented by the General Formula (1) or (2), the ligands $Y^1$ and $Y^2$ may be relatively easy substituted or desorbed depending on the type thereof. As an example, ligands in a chloro complex represented by the Formula (4) are exchanged with water molecules in water to thereby produce an aqua complex represented by the Formula (5), as shown in the following scheme. Then, the aqua complex represented by the Formula (5) is deprotonated under a basic condition to thereby produce an oxo complex represented by the Formula (6).

The aqua complex represented by the Formula (5) is easily converted to a hydride complex represented by the Formula (7) in the presence of hydrogen gas or formic acid/formic acid salt.

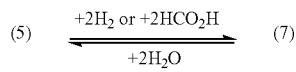

The chloro complex represented by the Formula (4) is, in heavy water, converted to a complex represented by the Formula (9) in which ligands are substituted with heavy water molecules (-D$_2$O, -T$_2$O), or is deprotonated under a basic condition to thereby produce a heavy-hydrogenated oxo complex (—OD, —OT), and then, easily converted to a deuteride complex (10) in the presence of hydrogen gas or a formic acid molecule.

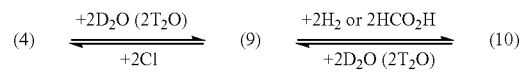

When the complex represented by any of the Formulae (1) to (10) has an isomer such as a tautomer or a stereoisomer (e.g., a geometric isomer, a conformational isomer, and an optical isomer), the isomer also can be used in the present invention. For example, considered are two isomers in which pairs of ligands $L^1$ and $L^2$ and $Y^1$ and $Y^2$ being coordinated to metals are in a cis- or a trans-configuration.

In the complex represented by any of the Formulae (1) to (3), for example, m is preferably 0 to 5, more preferably 2, 3, or 4.

In the multinuclear complexes represented by any of the Formulae (1) to (10), a counter ion thereof is not particularly limited. Examples of an anion serving as the counter ion include a hexafluorophosphate ion (PF$_6^-$), a tetrafluoroborate ion (BF$_4^-$), a hydroxide ion (OH$^-$), an acetate ion, a carbonate ion, a phosphate ion, a sulfate ion, a nitrate ion, a halide ion (e.g., a fluoride ion (F$^-$), a chloride ion (Cl$^-$), a bromide ion (Br$^-$), and an iodide ion I$^-$), a hypohalite ion (e.g., a hypofluorite ion, a hypochlorite ion, a hypobromite ion, and a hypoiodite ion), a halite ion (e.g., a fluorite ion, a chlorite ion, a bromite ion, and an iodite ion), a halate ion (e.g., a fluorate ion, a chlorate ion, a bromate ion, and an iodate ion), a perhalate ion (e.g., a perfluorate ion, a perchlorate ion, a perbromate ion, and a periodate ion), a trifluoromethanesulfonate ion (OSO$_2$CF$_3^-$), and a tetrakis(pentafluorophenyl)borate ion [B(C$_6$F$_5$)$_4^-$]. Examples of a cation serving as the counter ion include, but are not limited to, various metal ions, such as a lithium ion, a magnesium ion, a sodium ion, a potassium ion, a calcium ion, a barium ion, a strontium ion, an yttrium ion, a scandium ion, and a lanthanoid ion; and a hydrogen ion. Although these counter ions may be present alone, or two or more of these counter ions may be concomitantly present. However, the above description is intended to only exemplify possible mechanisms, and the present invention is not limited thereto.

Notably, the alkyl group is not particularly limited in the present invention. Examples thereof include a methyl group, an ethyl group, an n-propyl group, an isopropyl group, an n-butyl group, an isobutyl group, a sec-butyl group and a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. With regard to a group and an atomic group (e.g., an alkoxy group) derived from the alkyl group, examples of the alkyl group are the same as the above mentioned group. The alcohol and the alkoxide ion are not particularly limited. Examples thereof include alcohols and alkoxide ions derived from the aforementioned alkyl groups. Moreover, as used herein, "halogen" refers to any halogen element. Examples thereof include fluorine, chlorine, bromine, and iodine. In the present invention, in the case where a substituent has an isomer, any isomer may be used unless otherwise restricted. For example, a "propyl group" as referred to simply herein may be an n-propyl group or an isopropyl group. Also, a "butyl group" as referred to simply herein may be any of an n-butyl group, an isobutyl group, a sec-butyl group, and a tert-butyl group. However, the above description is intended to only exemplify possible mechanisms, and the present invention is not limited thereto.

[Catalyst for Dehydrogenation of Formic Acid]

A catalyst for dehydrogenation of formic acid of the present invention is a catalyst for dehydrogenation of formic acid containing, as an effective ingredient, a multinuclear metal complex represented by any of the Formulae (1) to (10), a tautomer or stereoisomer thereof, or a salt thereof. The effective ingredient of the catalyst for dehydrogenation consists of at least one compounds selected from the group consisting of a multinuclear metal complex represented by any of the Formulae (1) to (10), a tautomer thereof, a stereoisomer thereof, and a salt thereof. For example, one or more compounds serving as the effective ingredient may be used as-is as the catalyst for dehydrogenation of formic acid of the present invention, or a mixture of the above-described isomers may be used as the catalyst. Other ingredients may be appropriately added in addition to the compounds serving as the effective ingredient. Formic acid is dehydrogenated by the action of the catalyst for dehydrogenation of formic acid of the present invention to thereby generate hydrogen ($H_2$) and carbon dioxide ($CO_2$).

A method for dehydrogenating formic acid of the present invention includes at least one step selected from the group consisting of a step of stirring a solution containing the catalyst for dehydrogenation of formic acid of the present invention and formic acid and/or a formic acid salt, and a step of heating the solution. Specifically, for example, the formic acid and/or the formic acid salt are added to a solution of any of the compounds (1) to (10), and then, the resultant solution is left to stand and, as necessary, heated. In the case where the solution is heated, heating temperature is not particularly limited, but is, for example, 0° C. to 200° C., preferably 20° C. to 100° C., and more preferably 40° C. to 80° C. A method for collecting generated hydrogen is not particularly limited. For example, a known method such as a downward displacement of water method or an upward displacement method may be appropriately used.

In the method for dehydrogenating formic acid of the present invention, the solvent is not particularly limited. For example, the solvent may be water or an organic solvent, and one solvent may be used alone or two or more solvents may be used in combination. In the case where any of the compounds (1) to (10) is soluble in water, it is preferred to use water or heavy water from the viewpoint of a simple procedure. The organic solvent is not particularly limited, but a highly polar solvent is preferable from the viewpoint of solubility of the catalyst. Examples thereof include nitriles such as acetonitrile, propionitrile, butyronitrile, or benzonitrile; primary alcohols such as methanol, ethanol, n-propyl alcohol, or n-butyl alcohol; secondary alcohols such as isopropyl alcohol or s-butyl alcohol; tertiary alcohols such as t-butyl alcohol; polyhydric alcohols such as ethylene glycol or propylene glycol; ethers such as tetrahydrofuran, dioxane, dimethoxyethane, or diethyl ether; amides such as dimethylformamide or dimethylacetamide; sulfoxides such as dimethyl sulfoxide; and esters such as ethyl acetate. Furthermore, formic acid as a raw material may be in the form of a solution or a salt.

In the method for dehydrogenating formic acid of the present invention, a concentration of any of catalysts represented by the compounds (1) to (10) in the solution is not particularly limited, but, for example, 0.0001 mmol/L to 50 mmol/L, preferably 0.005 mmol/L to 20 mmol/L.

In the method for dehydrogenating formic acid and a method for producing hydrogen of the present invention, a ratio of amount of substance (the number of molecules) of catalyst molecules to that of formic acid molecules is not particularly limited, but, for example, the ratio formic acid molecules catalyst molecules is 100:1 to 1:100,000,000 at the start of the reaction. Hydrogen can be continuously produced by additionally adding or continuously adding dropwise formic acid molecules during the reaction. As used herein, a formic molecule includes formic acid and a formic acid salt, which may be used alone or as a mixture thereof. In the case where the mixture is used, it is generally used in a pH range of 1 to 9, but formic acid may be dehydrogenated at a pH out of the above range by additionally adding an acid or a base. In the case where the formic acid salt is used alone, examples of a counter cation include, but not limited thereto, various metal ions such as a lithium ion, a magnesium ion, a sodium ion, a potassium ion, a calcium ion, a barium ion, a strontium ion, an yttrium ion, a scandium ion, or a lanthanoid ion; an ammonium ion, tetramethyl ammonium, and tetraethyl ammonium. Although these counter ions may be present alone, or two or more of these counter ions may be concomitantly present.

In the method for dehydrogenating formic acid or the method for producing hydrogen of the present invention, formic acid is dehydrogenated typically under atmospheric pressure to thereby produce carbon dioxide gas and hydrogen gas having atmospheric pressure. In the case where a sealed reaction container is used, the reaction container may be pressurized by the produced gas. A gas pressure in the reaction container is not particularly limited, but is, for example, 0 MPa to 100 MPa, preferably 1 MPa to 10 MPa. The dehydrogenation reaction of formic acid is not interfered even under high pressure and generates the gas. Accordingly, as the progression of the reaction, pressure inside of the reaction container is spontaneously increased, which allows high pressure hydrogen gas to be spontaneously supplied without pressurizing by means of external energy.

The catalyst for dehydrogenation of formic acid of the present invention significantly accelerates the dehydrogenation of formic acid by the concerted action of two metals. For example, a mononuclear iridium catalyst represented by the following Formula (11) which has a structure similar to the multinuclear iridium catalyst represented by the Formula (4) exhibits almost no catalyst performance. Compared to the dehydrogenation reaction of formic acid or the method for producing hydrogen isotope gas using the mononuclear catalyst described in PTL 2 or 8, which is similar to the present invention, it has been found that the multinuclear iridium catalyst of the present invention has obviously excellent performance than the mononuclear catalyst. As can be seen from the above results, two metals are needed to accelerate the dehydrogenation of formic acid.

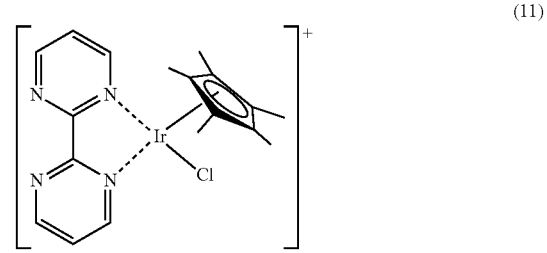

(11)

The catalyst of the present invention can be used as a catalyst for dehydrogenation of formic acid in, for example, a formic acid fuel cell. In the case where the catalyst is used in the fuel cell, for example, it is sufficient that the cell contains the catalyst for dehydrogenation of formic acid of the present invention and includes therein a mechanism for generating hydrogen by dehydrogenating formic acid according to the above described method. A specific configuration of the fuel cell is not particularly limited, and, for example, a configuration of a known fuel cell can be appropriately applied thereto. Furthermore, the application of the catalyst for dehydrogenation of formic acid of the present invention is not limited to those mentioned above, and, for example, the catalyst for dehydrogenation of formic acid according to the present invention can be used in every technical field in which hydrogen ($H_2$) is needed to be supplied.

(Method for Producing Heavy Hydrogen Gas or Heavy-Hydrogenated Hydrogen)

In a method for producing heavy hydrogen gas or heavy-hydrogenated hydrogen of the present invention, used is a catalyst consists of an isolated compound serving as an effective ingredient selected from the group consisting of a multinuclear metal catalyst represented by the General Formula (1), a tautomer thereof, a stereoisomer thereof, and a salt thereof or a mixture thereof; or a catalyst containing the compound serving as the effective ingredient. In the present invention, hydrogen isotope gas can be produced from an aqueous solution of formic acid in which formic acid (formic acid salt), water, or both thereof is heavy-hydrogenated.

In the method for producing heavy hydrogen gas or heavy-hydrogenated hydrogen of the present invention, in the case where heavy formic acid and/or heavy formic acid salt are used, they are generally used in a pH range of 1 to 9, but formic acid may be dehydrogenated at a pH out of the above range by additionally adding an acid or a base.

EXAMPLES

Hereinafter, examples of the present invention will be described in more detail. However, the present invention is not limited to the following examples.

Catalyst Synthesis 1

To methanol (20 mL), were added commercially available 2,2'-bipyrimidine (79 mg) and dicyclo(pentamethylcyclopentadienyl)iridium(III) dimer (398 mg), followed by stirring at 40° C. for 12 hours. The insoluble matter was filtered off, and the filtrate was distilled off under reduced pressure to thereby obtain a chloride of a cis/trans mixture (4:5) represented by the Formula (4) which is stable in the air. The spectral data of the resultant catalyst is shown below.

$^1$H NMR (400 MHz, $D_2O$) 6 (DSS, ppm) Cis form: 9.61 (d, J=5.8 Hz, 4H), 8.46 (dd, J=5.8, 5.8 Hz, 4H), 1.75 (s, $C_5Me_5$, 30H). Trans form: 9.55 (d, J=5.8 Hz, 4H), 8.41 (dd, J=5.8, 5.8 Hz, 4H), 1.79 (s, $C_5Me_5$, 30H).

Example 1

A solution of the chloride of the multinuclear iridium complex (4) (cis- and trans-mixture) produced in Catalyst synthesis 1 (9.6 mg) in water (2 mL) was degassed. To a degassed solution of 1 M formic acid/sodium formate (1:1) in water (10 mL) with stirring at 60° C., was added the above prepared catalyst solution (100 μL, 0.5 μmol), and immediately thereafter, the resultant solution was changed in color to violet, which is a characteristic color of iridium (I). The change in color was strongly suggested that the compound corresponding to the Formula (8) was produced. A gas yield was measured by means of a gas meter (Shinagawa W-NK-05) (FIG. 1). As a result, the turnover frequency of the catalyst was 32,000 per 1 hour, which indicated the best catalyst performance in the world at this reaction temperature. A generated gas component was measured by means of a gas chromatography GL SCIENCES (GC390), hydrogen was measured by means of a thermal conductivity detector (TCD), and carbon dioxide and carbon monoxide were measured by means of a methanizer and a flame ionization detector (FID). As a result, it was found that hydrogen and carbon dioxide were generated in a ratio of 1:1, and that carbon monoxide was not detected (below the detection threshold of 10 ppm). Seven hours later, a concentration of the formic acid molecules in the reaction solution was measured by means of a high-performance liquid chromatography. Specifically, the reaction solution was passed through a column (TSKgel SCX (H+): TOSOH) using a 2 mM phosphate aqueous solution as a developing solution, and the resultant flow-through was measured at a wavelength of 210 nm. It was found that the concentration was 0.5 M. From these results, it was found that the dehydrogenation reaction efficiently progressed in an amount corresponding to that of formic acid.

Example 2

Figure 2:
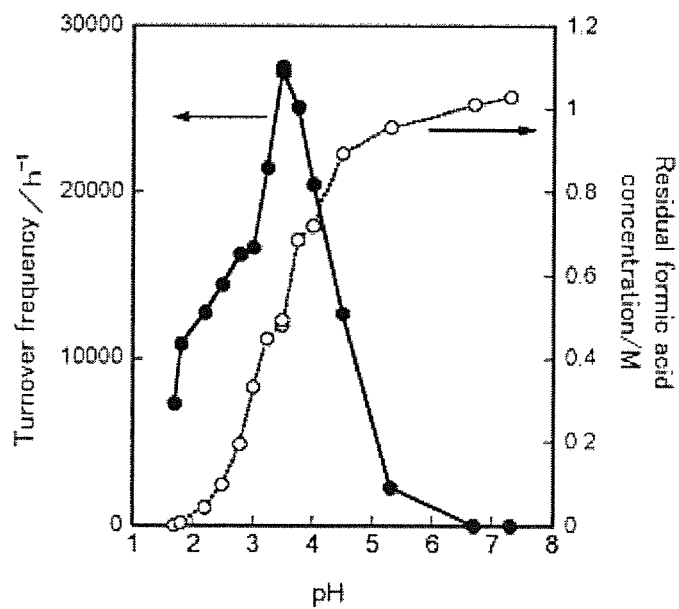
FIG. 2 is a graph representing the turnover frequency ($h^{-1}$) of a catalyst for dehydrogenation of formic acid of Example in an aqueous solution of 1 M formic acid/sodium formate containing the catalyst, and a pH dependence of a concentration of formic acid remaining in a reaction solution after the completion of a reaction.

A solution of the chloride of the multinuclear iridium complex (4) (cis- and trans-mixture) produced in Catalyst synthesis 1 (9.6 mg) in water (2 mL) was degassed. To a degassed solution of 1 M formic acid/sodium formate in water (10 mL) of which pH had been adjusted, was added the above prepared catalyst solution (100 μL, 0.5 μmol), followed by stirring at 60° C. The turnover frequencies (TOF) per 1 molecule of the catalyst per 1 hour at varying pH values, and the concentrations of formic acids remaining after the completion of the reaction were shown in FIG. 2. As a result, it was found that the catalyst had the highest activity at a pH range of 2.5 to 4, in particular, at a pH of about 3.5, and that the catalyst had a sufficiently high activity even at a pH of about 1.8, at which formic acid was used alone, and almost no formic acid remained after the reaction. From these results, it was found that the dehydrogenation reaction efficiently progressed in an amount corresponding to that of formic acid.

Example 3-1

A solution of the chloride of the multinuclear iridium complex (4) (cis- and trans-mixture) produced in Catalyst synthesis 1 (9.6 mg) in water (2 mL) was degassed. To a degassed solution of 1 M formic acid/sodium formate in water (30 mL) of which pH had been adjusted, was added the above prepared catalyst solution (100 μL, 0.5 μmol), followed by stirring at 80° C. It was found that the turnover frequency (TOF) per 1 molecule of the catalyst per 1 hour was 102,000 per hour, and that the concentration of formic acid remaining after the completion of the reaction was about 0.5 M.

Example 3-2

A solution of the chloride of the multinuclear iridium complex (4) (cis- and trans-mixture) produced in Catalyst synthesis 1 (9.6 mg) in water (2 mL) was degassed. To a degassed solution of 1 M formic acid/sodium formate in water (20 mL or 40 mL) of which pH had been adjusted, was added the above prepared catalyst solution (200 μL, 1 μmol), followed by stirring with heating. Reaction results are shown in Table 1.

TABLE 1

Dehydrogenation reaction of formic acid in the presence of multinuclear iridium complex (4)

| Solution amount/ mL | Catalyst concentration | Reaction period/ min | Reaction temperature/ °C. | TOF/h$^{-1}$ | TON | Residual formic acid concentration/ M |
|---|---|---|---|---|---|---|
| 20 | 50 μM | 150 | 50 | 11,900 | 10,100 | 0.495 |
| 20 | 50 μM | 90 | 60 | 27,600 | 10,400 | 0.48 |
| 40 | 25 μM | 60 | 70 | 59,000 | 20,200 | 0.495 |
| 40 | 25 μM | 30 | 80 | 107,000 | 20,200 | 0.495 |

Reaction solution: 1 M HCOOH/HCOONa (1:1), pH 3.5

Example 4-1

A solution of the chloride of the multinuclear iridium complex (4) (cis- and trans-mixture) produced in Catalyst synthesis 1 (9.6 mg) in water (2 mL) was degassed. To a degassed solution of 2 M formic acid in water (10 mL), was added the above prepared catalyst solution (100 μL, 0.5 μmol), followed by stirring in the autoclave at 60° C. After stirring for 8 hours, the pressure in the reaction container was found to be 1.2 MPa.

Example 4-2

Figure 3:
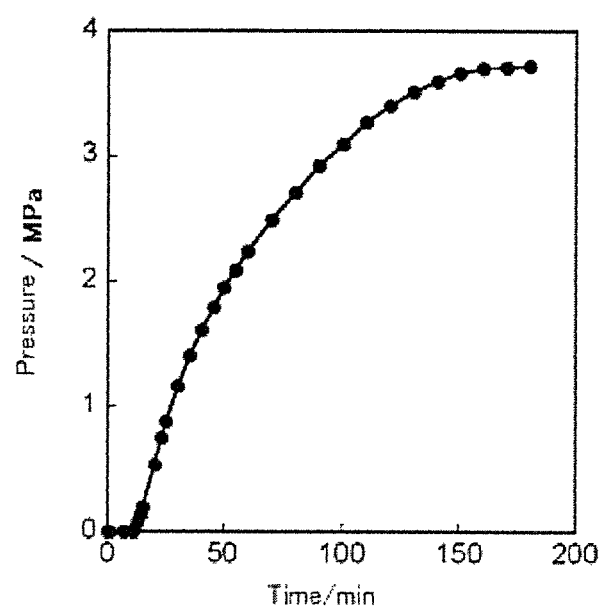
FIG. 3 is a graph representing a change in pressure over time in a sealed glass autoclave containing an aqueous solution of 1 M formic acid and a catalyst for dehydrogenation of formic acid of Example.

To the chloride of the multinuclear iridium complex (4) (cis- and trans-mixture) produced in Catalyst synthesis 1 (9.6 mg), was added a degassed solution of 1 M formic acid in water (10 mL), followed by stirring in a sealed glass autoclave at 60° C. Pressures in the reaction container were shown in FIG. 3. After stirring for 7 hours, the pressure in the reaction container reached to 3.7 MPa. The concentration of formic acid remaining in the reaction solution was found to be 7.3 mM, which indicates that 99.3% of formic acid could be decomposed.

Example 5

A solution of the chloride of the multinuclear iridium complex (4) (cis- and trans-mixture) produced in Catalyst synthesis 1 (9.6 mg) in deuterium water (D$_2$O) (2 mL) was degassed. To a degassed solution of 1 M formic acid/sodium formate (1:1) in heavy water (10 mL), was added the above prepared catalyst solution (200 μL, 1 μmol), followed by stirring at 60° C. The generated hydrogen, deuterated hydrogen, and deuterium were subjected to GC analysis using a thermal conductivity detector (TCD) and an isotope gas separation column (HYDRO ISOPAK, GTR TEC Co., Ltd.). Results are shown below.
Hydrogen: 2.8%
Deuterated hydrogen: 78.5%
Deuterium: 18.7%
Carbon monoxide: not detected (below the detection threshold of 10 ppm)

Example 6

A solution of the chloride of the multinuclear iridium complex (4) (cis- and trans-mixture) produced in Catalyst synthesis 1 (9.6 mg) in deuterium water (D$_2$O) (2 mL) was degassed. To a degassed solution of 1 M heavy formic acid/heavy sodium formate (1:1) in heavy water (10 mL), was added the above prepared catalyst solution (200 μL, 1 μmol), followed by stirring at 60° C. Percentages of the generated hydrogen isotope gases are shown below.
Hydrogen: 0%
Deuterated hydrogen: 1.9%
Deuterium: 98.1%
Carbon monoxide: not detected (below the detection threshold of 10 ppm)

Example 7

The compound represented by the following Formula (12) was synthesized using dichloro(pentamethylcyclopentadienyl)rhodium(III) dimer according to Catalyst synthesis 1. To a degassed solution of 1 M formic acid/sodium formate (1:1) in water (10 mL), was added the chloride of the multinuclear rhodium complex represented by the following Formula (12) (3.9 mg, 5 μmol), followed by stirring at 60° C. The gas yield was measured and it was found that the turnover frequency (TOF) per 1 molecule of the catalyst per 1 hour was 1,200 per hour.

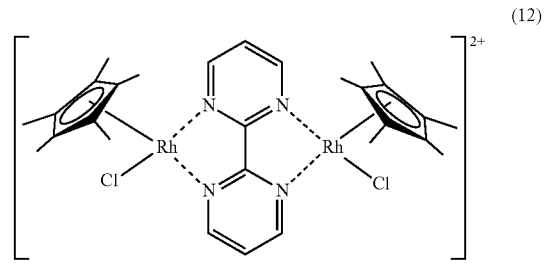

(12)

Example 8

The compound represented by the following Formula (13) was synthesized using dichloro(hexamethylbenzene)ruthenium(II) dimer according to Catalyst synthesis 1. To a degassed solution of 1 M formic acid/sodium formate (1:1) in water (10 mL), was added the chloride of the multinuclear ruthenium complex represented by the following Formula (13) (3.5 mg, 4 μmol), followed by stirring at 60° C. It was confirmed that a gas was generated in the reaction solution.

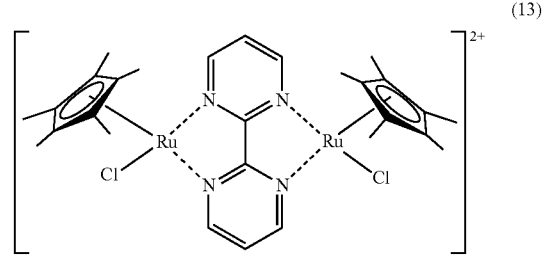

(13)

Comparative Example 1

A catalyst consisting of chloride of mononuclear iridium complex represented by the following Formula (11) which has a structure similar to those represented by the above Formula (4) was synthesized dimer according to NPL 12. A solution of the chloride of the mononuclear iridium complex represented by the following Formula (11) (5.6 mg) in water (2 mL) was degassed. To a degassed solution of 1 M formic acid/sodium formate (1:1) in water (10 mL, pH 3.5), was added the above prepared catalyst solution (100 μL, 0.5 μmol), followed by stirring at 60° C. However, the gas yield was below the measurement threshold.

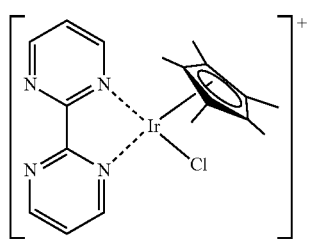

(11)

INDUSTRIAL APPLICABILITY

The present invention allows hydrogen gas ($H_2$), heavy hydrogen gas ($D_2$, $T_2$) or heavy-hydrogenated hydrogen (HD, HT) to be produced in a highly efficient, simple, and inexpensive manner. That is, formic acid can be utilized as a hydrogen storage material, and be efficiently dehydrogenated by the action of a catalyst for dehydrogenation of formic acid of the present invention to thereby produce hydrogen. The catalyst for dehydrogenation of formic acid of the present invention can be easily prepared since it contains a catalyst ligand which is inexpensively commercially available. The dehydrogenation reaction is a selective reaction, so that hydrogen can be obtained without by-producing carbon monoxide. Therefore, hydrogen can be supplied as fuel for a fuel cell without employing a gas reforming device.

Hydrogen isotope gas can be supplied in a simple and inexpensive manner due to the use of heavy formic acid and/or heavy water.

The invention claimed is:

1. A catalyst for dehydrogenation of formic acid, comprising:

a multinuclear metal complex represented by the following Formula (1), a tautomer or stereoisomer thereof, or a salt thereof,

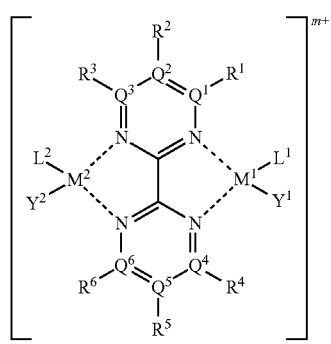

(1)

wherein $M^1$ and $M^2$ denote transition metals and may be the same as or different from each other;

$Q^1$ to $Q^6$ each independently denote carbon or nitrogen;

$R^1$ to $R^6$ each independently denote a hydrogen atom, an alkyl group, a phenyl group, a nitro group, a halogen group, a sulfonate group (sulfo group), a carboxylate group (carboxy group), an alkoxy group, an alkyl amino group, provided that when $Q^i$ is nitrogen, $R^i$ is absent at a position corresponding to the nitrogen;

$L^1$ and $L^2$ each independently denote a cyclopentadienyl ligand or a benzene ligand, and may be unsubstituted or substituted by one or more substituents;

$Y^1$ and $Y^2$ each independently denote any ligand or are absent; and m denotes a positive integer, 0, or a negative integer.

2. The catalyst for dehydrogenation of formic acid according to claim 1, wherein $M^1$ and $M^2$ each independently denote iridium, rhodium, ruthenium, cobalt, osmium, nickel, iron, palladium or platinum.

3. The catalyst for dehydrogenation of formic acid according to claim 1, wherein $M^1$ and $M^2$ denote iridium.

4. The catalyst for dehydrogenation of formic acid according to claim 1, wherein $L^1$ and $L^2$ each independently denote pentamethylcyclopentadienyl or hexamethylbenzene.

5. The catalyst for dehydrogenation of formic acid according to claim 1, wherein $Y^1$ and $Y^2$ each independently denote a water molecule, a hydrogen atom, a heavy hydrogen atom, an alkoxide ion, a hydroxide ion, a halide ion, a carbonate ion, a trifluoromethanesulfonate ion, a sulfate ion, a nitrate ion, a formate ion, or an acetate ion, or are absent.

6. The catalyst for dehydrogenation of formic acid according to claim 1, wherein the multinuclear metal complex represented by the Formula (1) is a multinuclear metal complex having a structure represented by the following Formula (2),

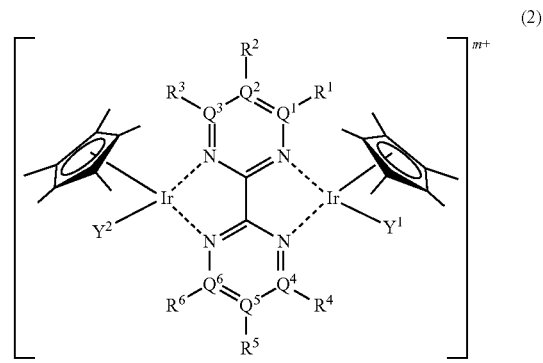

(2)

wherein $Q^1$ to $Q^6$, $R^1$ to $R^6$, $Y^1$, $Y^2$ and m are the same as in the Formula (1).

7. The catalyst for dehydrogenation of formic acid according to claim 6, wherein all of $Q^1$ to $Q^6$ denote carbon atoms.

8. The catalyst for dehydrogenation of formic acid according to claim 6, wherein all of $R^1$ to $R^6$ denote hydrogen atoms.

9. The catalyst for dehydrogenation of formic acid according to claim 6, wherein the multinuclear metal complex represented by the Formula (2) is a multinuclear metal complex represented by the following Formula (3),

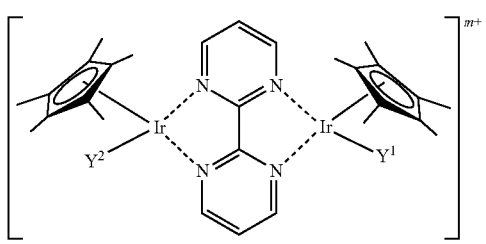
(3)

wherein $Y^1$, $Y^2$ and m are the same as in the Formula (2).

10. The catalyst for dehydrogenation of formic acid according to claim 9, wherein the multinuclear metal complex represented by the Formula (3) is one or more of multinuclear metal complexes represented by the following Formulae (4) to (10),

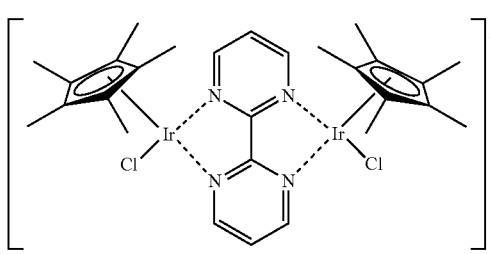
(4)

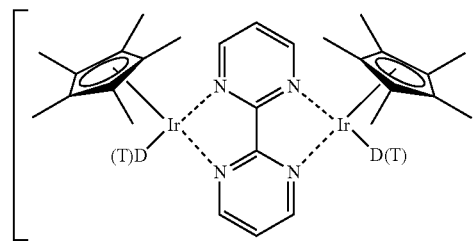
(5)

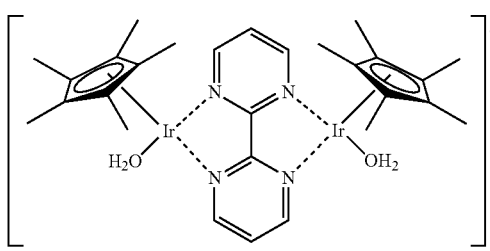
(6)

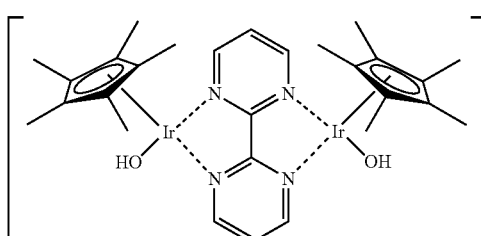
(7)

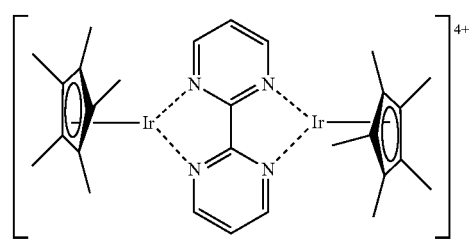
(8)

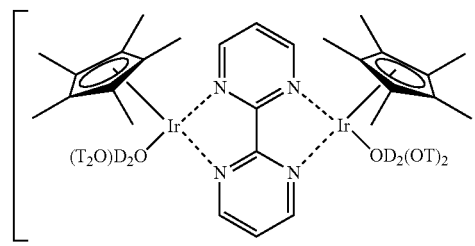
(9)

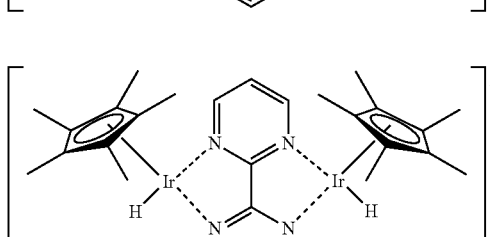
(10)

11. A method for dehydrogenating formic acid, comprising:
allowing a solution containing formic acid and/or a formic acid salt to react in the presence of the catalyst for dehydrogenation of formic acid according to claim 1, to thereby dehydrogenate formic acid.

12. A method for producing hydrogen gas ($H_2$) through dehydrogenation of formic acid, comprising:
allowing a solution containing formic acid and/or a formic acid salt to react in the presence of the catalyst for dehydrogenation of formic acid according to claim 1, to thereby produce hydrogen gas ($H_2$).

13. The method for dehydrogenating formic acid according to claim 11, wherein heavy hydrogen gas ($D_2$, $T_2$), heavy-hydrogenated hydrogen gas (HD, HT), or both thereof is produced using deuterium water ($D_2O$) and/or tritium water ($T_2O$) as a solvent of the solution.

14. The method for dehydrogenating formic acid according to claim 11, wherein heavy hydrogen gas ($D_2$, $T_2$), heavy-hydrogenated hydrogen gas (HD, HT), or both thereof is produced using deuterated formic acid (DCOOD) as the formic acid and/or deuterated formic acid salt ($DCOO^-$) as the formic acid salt.

15. The method for dehydrogenating formic acid according to claim 11, wherein heavy hydrogen gas ($D_2$, $T_2$) is produced using deuterated formic acid (DCOOD) as the formic acid and/or deuterated formic acid salt ($DCOO^-$) as the formic acid salt, and deuterium water ($D_2O$) and/or tritium water ($T_2O$) as the solvent.

16. The method for dehydrogenating formic acid accordingly to claim 11, wherein hydrogen gas, heavy hydrogen gas ($D_2$, $T_2$), or heavy-hydrogenated hydrogen gas (HD, HT) pressurized in a reaction container of which internal pressure is 0.1 MPa or more is produced.

17. The method for producing hydrogen has (H$_2$) through dehydrogenation of formic acid according to claim 12, wherein the hydrogen gas pressurized in a reaction container of which internal pressure is 0.1 MPa or more is produced.

\* \* \* \* \*